(12) United States Patent
Lee

(10) Patent No.: US 8,840,597 B2
(45) Date of Patent: Sep. 23, 2014

(54) ABSORBENT ARTICLE FOR MEDICAL TREATMENT OR MENSTRUATION

(76) Inventor: Chang Hoen Lee, Gwangju (KR)

( * ) Notice: Subject to any disclaimer, the term of this patent is extended or adjusted under 35 U.S.C. 154(b) by 80 days.

(21) Appl. No.: 13/382,513

(22) PCT Filed: Jun. 22, 2010

(86) PCT No.: PCT/KR2010/004017
§ 371 (c)(1),
(2), (4) Date: Jan. 5, 2012

(87) PCT Pub. No.: WO2011/004975
PCT Pub. Date: Jan. 13, 2011

(65) Prior Publication Data
US 2012/0101462 A1    Apr. 26, 2012

(30) Foreign Application Priority Data
Jul. 6, 2009    (KR) .................. 10-2009-0061367

(51) Int. Cl.
*A61F 13/20*    (2006.01)
(52) U.S. Cl.
USPC .................. 604/385.17; 604/385.18; 604/904
(58) Field of Classification Search
USPC .................. 604/385.17, 385.18, 904
See application file for complete search history.

(56) References Cited

U.S. PATENT DOCUMENTS

| | | | |
|---|---|---|---|
| 2,926,667 A | 3/1960 | Burger, Jr. et al. | |
| 3,854,481 A | 12/1974 | Messing | |
| 3,986,511 A * | 10/1976 | Olofsson et al. | 604/385.18 |
| 2004/0193131 A1 | 9/2004 | Wada | |
| 2005/0096620 A1 | 5/2005 | Awolin et al. | |
| 2007/0073257 A1 * | 3/2007 | Buck et al. | 604/385.18 |

FOREIGN PATENT DOCUMENTS

| | | |
|---|---|---|
| CN | 101351177 A | 1/2009 |
| KR | 19990083965 | 12/1999 |
| KR | 10-2001-0015128 | 2/2001 |
| KR | 10-2001-0072059 | 7/2001 |
| KR | 2002-0016858 | 3/2002 |
| KR | 100460253 | 12/2004 |
| KR | 10-2005-0012810 | 2/2005 |
| KR | 10-2005-0120638 | 12/2005 |
| KR | 10-2008-0091117 | 10/2008 |

OTHER PUBLICATIONS

International Search Report for PCT/KR2010/004017 mailed Mar. 24, 2011.

* cited by examiner

*Primary Examiner* — Jacqueline F. Stephens
(74) *Attorney, Agent, or Firm* — AKC Patents LLC

(57) ABSTRACT

The present invention relates to an absorbent fabric for medical treatment or menstruation, and more particularly, to a convenient and sanitary absorbent article to be used as a tampon, a blood-absorbing fabric for surgery, etc. The present invention provides an absorbent article for medical treatment or menstruation, wherein a flat absorbent article is provided with removal means and is formed into a cylindrical shape. The flat absorbent article is formed by forming an absorbent layer on a liquid passage layer. The removal means is arranged to cover the liquid passage layer and the absorbent layer of the flat absorbent article in the widthwise direction, and a portion of the removal means is outwardly exposed from the flat absorbent article in the widthwise direction of the flat absorbent article. The flat absorbent article is wound in the lengthwise direction and thus is formed into a cylindrical absorbent article, thereby fixing the removal means in the cylindrical absorbent article.

8 Claims, 5 Drawing Sheets

ABSORBENT ARTICLE FOR MEDICAL TREATMENT OR MENSTRUATION

RELATED APPLICATIONS

This application is a 371 application of International Application No. PCT/KR2010/004017, filed Jun. 22, 2010, which in turn claims priority from Korean Patent Application No. 10-2009-0061367, filed Jul. 6, 2009, each of which is incorporated herein by reference in its entirety.

TECHNICAL FIELD

The present invention relates to an absorbent fabric for a medical treatment or menstruation, and more particularly, to a convenient and sanitary absorbent article to be used as a tampon, a blood-absorbing fabric for surgery, etc.

BACKGROUND ART

Two basic types of tampons are widely used for a woman's sanitary purpose.

The first basic type is a finger type tampon which can be inserted into a vagina by using fingers, and the second basic type is an ordinary tampon which can be inserted with the aid of a certain insertion tool.

The two types of the tampons are manufactured in a longitudinal article called Softwind in such a way to fold the strips of an absorbent article loosely engaged.

A pledget is manufactured by compressing the Softwind in a radial shape and/or a two-axis shape.

In the above-mentioned two type of tampons, a pulling string is connected to the Softwind before or after the compression, thus easily pulling the tampon out of a users vagina after the tampon absorbed a predetermined amount of body fluid such as blood.

As shown in FIG. 1, a conventional tampon is configured in such a way that a flat absorbent article 100 is formed in a cylindrical shape, and a string 300 is sewed along a center line 200 of the flat absorbent article 100, so the string 300 can be used when a user pulls a tampon out of a user's vagina. So, a user pulls a tampon out of her vagina and disposes the tampon in a proper way.

In the course of the manufacture, the portions between the string 300 and the absorbent article 100 are interconnected by means of a sewing way. If a sewed portion is defective, the string might be disconnected from the absorbent article as a user pulls the string 300, which unfortunately makes the absorbent article 100 remain in the interior of a vagina.

The above conventional tampon is characterized in that an absorption layer generally made from a fiber material is placed on a penetration layer which allows liquid to penetrate, and another penetration layer is placed at an upper side of the absorbent article, and the thusly manufactured article is cut, thus manufacturing an absorbent article 100. The center line 200 of the absorbent article 100 and the string 300 are sewed together, thus manufacturing a tampon in a cylindrical shape.

When a tampon is actually used in a users vagina, the cylindrical absorbent article 100 is expanded in a flat shape. The fiber at the cut surface formed as a fiber forming an absorbent layer in the interior of the absorbent article 100 is cut, namely, the fiber at the cut surface formed as it is separated in a direction of the side portions of the absorbent article 100 might remain in the vagina, which makes a user feel uneasy during the use of the conventional tampon.

Linen (cotton fabric) is generally used as a fabric for surgery of a patient during a surgical operation. The linen is repeatedly used following washing and disinfection. The patients might be however exposed to pollutions or contaminations owing to bacteria in the fluid remaining after the linen is washed and disinfected. When a lot of fluid exists, it is almost impossible to properly control a lot of the fluid (absorption and external pollutant interruption) in the curse of actual use.

A disposable multilayer surgical operation fabric 400 made from a sanitary nonwoven fabric as shown in FIG. 2 is developed and used now in order to reduce the consumption of a non-sanitary linen surgical operation fabric. The above disposable surgical operation fabric still has a problem that it is impossible to control a lot of fluid at a time. The blood coming from during a surgical operation at a narrow portion cannot be properly eliminated, which prevents a surgical operation doctor to have a clear field of vision.

Part of the fiber might be separated from a disposable surgical operation fabric made from a nonwoven fabric during a surgical operation, so the part might be placed at an operation portion with it absorbed with blood or a surgical operation might be finished with a surgical operation fabric left behind after the surgical operation, which causes a medical accident.

REFERENCE INFORMATION OF CONVENTIONAL ART

Patent publication umber 10-2001-0104387
Patent registration number 10-0862331
Patent registration number 10-0940223
Patent publication number 10-2004-0070228
Utility model registration number 20-0310281
Patent registration number 10-0673915
Patent registration number 10-0460252

DISCLOSURE OF INVENTION

Accordingly, it is an object of the present invention to provide an absorbent article for a medical treatment or menstruation which overcomes the problems encountered in a conventional absorbent article for a medical treatment or menstruation and which is characterized in that an elimination part is positioned at a flat absorbent article in a surrounding shape, and the flat absorbent article is wound, thus forming a cylindrical absorbent article, so the elimination part is stably fixed by means of the winding of the flat absorbent article, not by the sewing, whereby it is possible to prevent the elimination part from being disconnected from the flat absorbent article.

The present invention is characterized in that a liquid penetration layer belonging to an flat absorbent article covers an absorption layer, which consequently makes it possible to prevent the fiber of the absorption layer from being separated or being left behind in a vagina or at a surgical operation portion.

The present invention is further characterized in that when an absorbent article is used as an absorption fabric for a surgical operation, it helps quickly absorb blood, and the elimination part serves to help easily remove the absorption fabric, so the absorption and elimination of blood can be easily performed with the aid of the use of the compressed absorbent article even when a surgical operation is performed at a narrow portion.

To achieve the above objects, there is provided an absorbent article for a medical treatment or menstruation which is formed of an elimination part at a flat absorbent article wherein the flat absorbent article is formed in a cylindrical shape, comprises a flat absorbent article being formed of an absorption layer disposed at an upper side of a liquid penetration layer, with the elimination part being disposed in such a way to cover in the widthwise direction the liquid penetration layer and the absorption layer of the flat absorbent article, with part of the same being exposed to one side of the widthwise direction of the flat absorbent article, as the flat absorbent article is wound in the longitudinal direction, thus being formed in a cylindrical absorbent article, with the elimination part is fixed at the cylindrical absorbent article.

ADVANTAGEOUS EFFECTS

In the present invention, the problems that an elimination part is easily disconnected from a menstruation tampon can be overcome. The fiber of an absorption layer in the interior of the absorbent article can be prevented from remaining in the interior of a vagina, which provides a user with a safe and sanitary use of tampon.

The present invention provides an absorbent article for an internal or surgical medical purpose which absorbent article is capable of quickly absorbing the blood from a surgical operation portion, and a compressed absorbent article can be inserted into a narrow surgical operation portion, which enables an easier use of product, and a surgical doctor has a clear field of vision in the course of a surgical operation, and an elimination can be simply done with the aid of an elimination part.

BRIEF DESCRIPTION OF THE DRAWINGS

The present invention will become better understood with reference to the accompanying drawings which are given only by way of illustration and thus are not limitative of the present invention, wherein.

BEST MODES FOR CARRYING OUT THE INVENTION

The preferred embodiments of the present invention will be described with reference to the accompanying drawings.

First of all, a cylindrical absorbent article 1a corresponding to an absorbent article for a medical treatment and menstruation according to the present invention comprises an absorption layer 11 made from an absorbent fiber material, and a liquid penetration layer 12.

Figure 6:
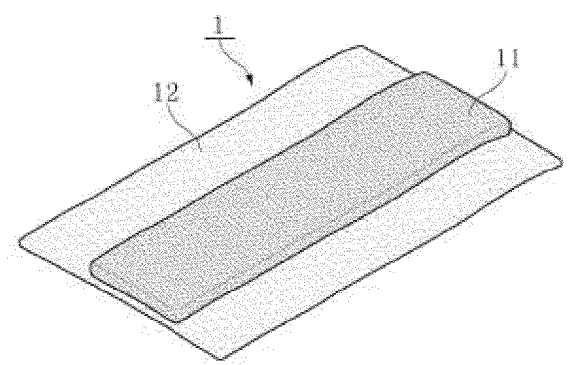
FIGS. 6 and 8 are perspective views illustrating a flat absorbent article according to the present invention.
Figure 10:
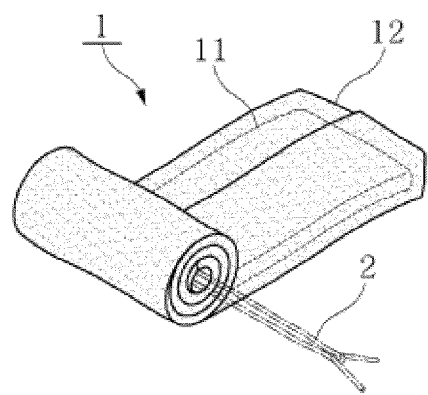
FIG. 10 is a view illustrating a state that a flat absorbent article is wound together with an elimination part according to the present invention.

As shown in FIG. 10, the cylindrical absorbent article 1a is formed as a flat absorbent article 1 is wound in a longitudinal direction. The flat absorbent article 1 as shown in FIGS. 6 and 8 is formed as an absorption layer 11 is placed at an upper side of the liquid penetration layer 12.

Figure 8:
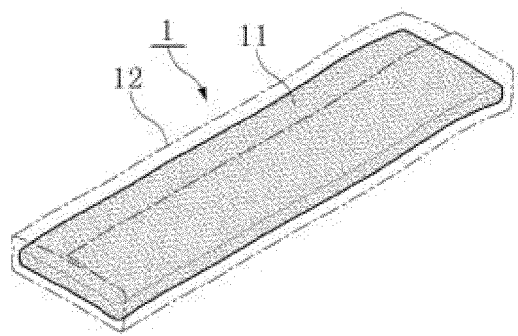

The liquid penetration layer 12 has a width wider than the absorption layer 11, and the absorption layer 11 is placed at a center portion of the liquid penetration layer 12, and as shown in FIG. 8, it is preferred that an upper end portion of the liquid penetration layer 12 is folded like it covers the absorption layer 11, and a lower end portion of the liquid penetration layer 12 is folded and overlapped like it covers the absorption layer 11.

Here, the sizes of the liquid penetration layer 12 and the absorption layer 11 are not limited thereto. The size is enough as long as its upper side is folded and overlapped over the lower side as the width of the liquid penetration layer 12 is larger than the width of the absorption layer 11.

The absorption layer 11 is made from a fiber web including an absorption fiber material or a hydrophilic fiber such as rayon, cotton, etc. and is covered by means of the liquid penetration layer 12, so it is possible to prevent an escape or separation of the fiber web of the absorption layer when in use.

It is preferred that the absorption layer 11 might be formed of, together with a hydrophilic fiber, a hydrophobic fiber or a hydrophobic fiber processed to have a hydrophilic feature, and a compound with an absorption function such as a high absorption polymer or the like might be combined with the same.

At this time, it is preferred that the absorption layer 11 is formed in such a way that a thin fiber web is overlapped in multiple layers; however the number and thickness of the same is not limited. It might be formed of one sheet of the fiber web.

The liquid penetration layer 12 is made from a hydrophobic fiber, for example, it is made from a spun lace, air through, point bond, spun bond, thermal bond nonwoven fabric or porous plastic sheet, etc. each being formed of a hydrophobic fiber such as polyester, polypropylene, polyethyleneterephthalate, etc., the kinds of which are not limited thereto.

MODES FOR CARRYING OUT THE INVENTION

Figure 7:
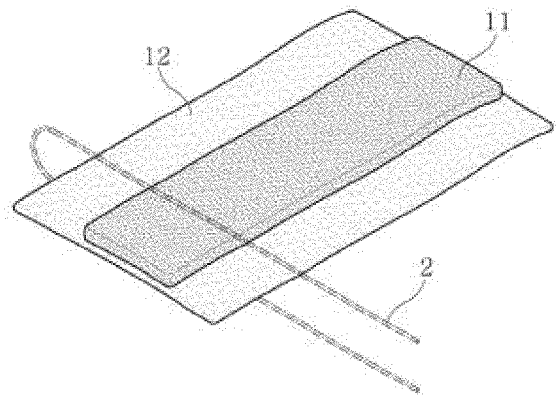
FIGS. 7 and 9 are views illustrating a state that an elimination part is installed at a flat absorbent article according to the present invention.
Figure 9:
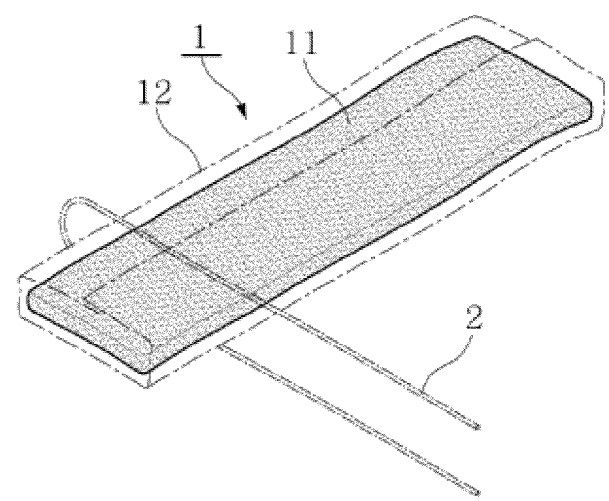

The thusly formed flat absorbent article 1 is equipped with an elimination part 2. As shown in FIGS. 7 and 9, the elimination part 2 covers in the widthwise direction the liquid penetration layer 12 and the absorption layer 11 of the flat absorbent article 1, with part of the same being exposed to one side of the widthwise direction of the flat absorbent article 1. As the flat absorbent article 1 is wound in the longitudinal direction, thus being formed as a cylindrical absorbent article 1a, so the elimination part 2 is fixed at the cylindrical absorbent article 1a.

Here an ordinary string is generally used as the elimination part 2. As shown in FIG. 6, since both ends of the string are exposed to one side of the flat absorbent article 1, in other words, to the rear end portion of a cylindrical absorbent article 1a to be formed, thus resulting in an easier use.

As shown in FIG. 9, the absorbent article can be used with both ends of the string being tied. The string exposed to one side is tied, and the flat absorbent article 1 is inserted in the longitudinal direction into the string, and part of the string tied is exposed to one side of the widthwise direction of the flat absorbent article 1.

As shown in FIG. 9, it is appreciated that the elimination part 2 might be installed with the upper and lower portions of the liquid penetration layer 12 being folded, in other words, with the absorption layer 11 being covered, and as shown in FIG. 7, it might be installed with the absorption layer 11 being positioned at the center of the liquid penetration layer 12, so the liquid penetration layer 12 as well as the elimination part 2 are installed in such a way to be foldable together.

The elimination part 2 is installed at one side of the longitudinal direction of the flat absorbent article 1, so it is preferably positioned at the center of the rear end of the wound cylindrical absorbent article 1a.

In the drawings of the present invention, a string is used as the elimination part 2; however it is obvious that the elimination part 2 can be made from a material same as the liquid penetration layer 12 in a sheet shape and can be equipped with a certain element.

The material of the elimination part 2 is not limited thereto, in other words, for easier convenience when in use, it might be made from a non-absorption material. In the event of absorption material, it is preferably needed for its outer surface to be waterproofed.

Not shown in the drawings, the flat absorbent article 1 might be formed to have embossed portions. With the liquid penetration layer 12 be folded, the flat absorbent article 1 is pressed to have an embossing part, which helps increase the surface area of the flat absorbent article 1 along with a faster absorption speed. The blood with a high viscosity can be effectively absorbed by means of the embossed structure.

Figure 1:
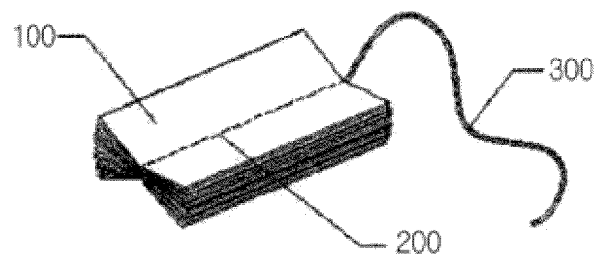
FIG. 1 is a view illustrating a conventional menstruation tampon.
Figure 2:
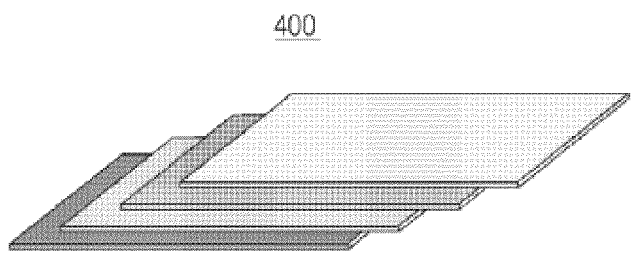
FIG. 2 is a view illustrating a conventional surgical operation absorption fabric.
Figure 3:
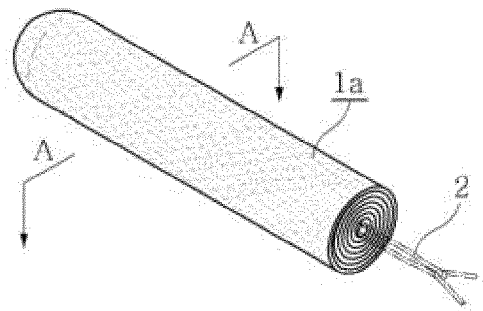
FIG. 3 is a perspective view illustrating an absorbent article for a medical treatment and menstruation purpose according to the present invention.
Figure 4:
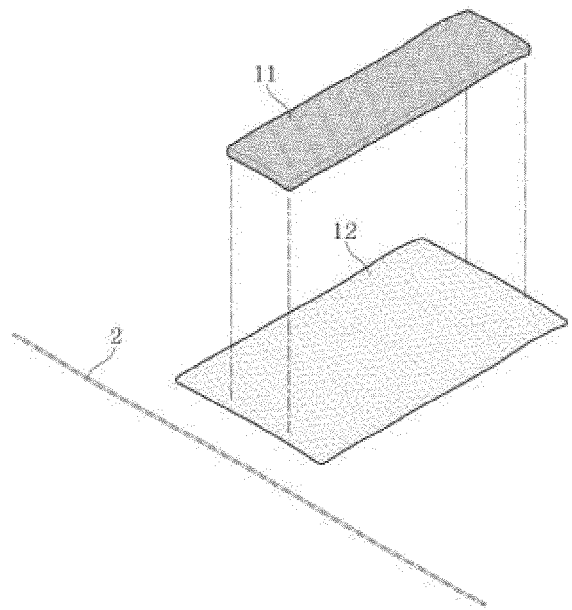
FIG. 4 is a disassembled perspective view illustrating an absorbent article for a medical treatment and menstruation purpose according to the present invention.
Figure 5:
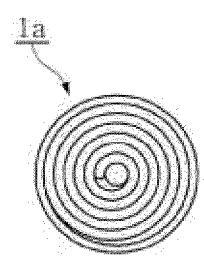
FIG. 5 is a cross sectional view taken along line A-A of FIG. 3.

As shown in FIG. 10, the flat absorbent article 1 is processed to be a cylindrical absorbent article 1a as it is wound from one end to the other end in a longitudinal direction. In the course of winding, it is processed to have a cylindrical shape while compressing with a certain pressure, thus manufacturing the cylindrical absorbent article 1a as shown in FIG. 3.

In the course of compression, as the flat absorbent article 1 is compressed as moisture is being supplied thereto, since the hydrogen coupling occurs between neighboring fibers, which prevents the original volume from recovering following the compression, a cylindrical absorbent article 1a remains unchanged even after the process.

As the cylindrical absorbent article 1a absorbs blood when in use, the volume keeping compressed due to the hydrogen coupling between fibers returns back to its original volume while expanding.

The size of the cylindrical absorbent article 1a is not limited. It is preferred that the size is enough as long as it is well inserted into the interior of a woman's vagina. The cylindrical absorbent article might be manufactured in various sizes for the use as a surgical operation absorption fabric, so it is preferred to select a certain size proper for a corresponding surgical operation portion.

The cylindrical absorbent article 1a can be used as a menstruation tampon or a surgical operation absorption fabric. In the course of the formation of the cylindrical absorption article 1a, the front portion of the cylindrical absorption article 1a might be formed in a circularly convex shape, not in a rectangular shape, in such a way that a higher pressure is applied to the front end portion or one end of the flat absorbent article 1, namely, the front end portion of the cylindrical absorption article 1a is formed to have a narrower width than the other end portion. So, the cylindrical absorbent article can be easily inserted into the vagina when in used as a tampon for menstruation. Even when it is used as an absorption fabric as a surgical operation, it can be easily inserted into a surgical operation portion.

Figure 11:
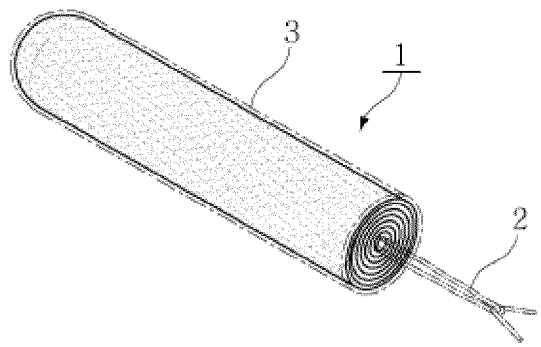
FIG. 11 is a view illustrating a state that an absorbent article for a medical treatment and menstruation.
Figure 12:
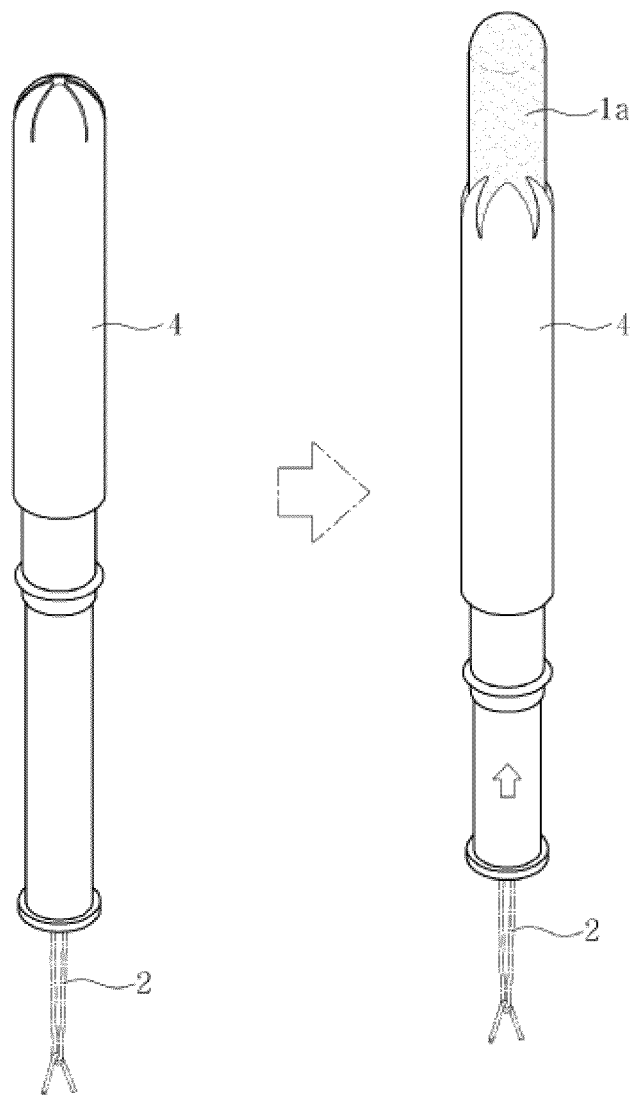
FIG. 12 is a view illustrating a state that an absorbent article for a medical treatment and menstruation is accommodated in an applicator according to the present invention.

As shown in FIG. 11, the cylindrical absorbent article 1a according to the present invention can be packed in a packing paper 3 for the use as a finger tampon or a surgical operation absorption fabric. As shown in FIG. 12, it can be encased in a tampon applicator 4 for the use as an applicator tampon. FIG. 12 shows only one kind of the tampon applicator 4; however any type of tampons currently available in the markets can be used for the purpose of a tampon insertion. It is obvious that it can be attached to or at an additional surgical operation instrument for the use of a surgical operation absorption fabric.

As described above, the present invention has been described with the above embodiments; however it is obvious that various modifications are available without escaping from the scopes and concepts of the present invention.

INDUSTRIAL APPLICABILITY

The present invention is directed to an absorbent article for a medical treatment and menstruation by providing a convenient, sanitary absorbent article which can be applied as a tampon for menstruation, a surgical operation blood absorption fabric, etc.

It is appreciated that the absorbent fabric according to the present invention improves a problem encountered in the conventional art that an elimination part used to be easily disconnected from a menstruation tampon, and effectively prevents part of the fiber of the absorption layer of the absorbent article from remaining in the interior of a vagina, which consequently results in a safe and sanitary use.

The absorbent article according to the present invention might be used as an absorbent article for an internal or surgical medical treatment, thus faster absorbing blood coming from a surgical portion, and since a compressed absorbent article can be inserted into a narrow surgical portion, a doctor can have a clear field of vision during a surgical operation.

The invention claimed is:

1. An absorbent article for a medical treatment or menstruation which is formed of an elimination part at a flat absorbent article wherein said flat absorbent article is formed in a cylindrical shape, comprising:

a flat absorbent article being formed of an absorption layer disposed at an upper side of a liquid penetration layer, with the width of the liquid penetration layer being wider than the width of the absorption layer, with the absorption layer being disposed at the center of the liquid penetration layer, with the upper and lower end portions of the liquid penetration layer extending beyond the top and bottom of the absorption layer, the upper and lower end portions being folded to entirely cover the absorption layer, thus preventing an escape of the inner absorption layer, with the flat absorbent article being embossed, with the elimination means being formed of a string and disposed in such a way to cover in the widthwise direction the liquid penetration layer and the absorption layer of the flat absorbent article, with both ends of the strip being exposed to one side of the widthwise direction of the flat absorbent article, as moisture is absorbed by the flat absorbent article, the moisture-absorbed flat absorbent article is compressed and wound in the longitudinal direction from its one end to the other end, thus being formed in a cylindrical absorbent article, with the strip being fixed to the cylindrical absorbent article, with the strip being positioned at one side of the longitudinal direction of the flat absorbent article and then being consequently positioned at the center of the rear end of the wound cylindrical absorbent article, wherein the absorption layer of the cylindrical absorbent article is enclosed by the liquid penetration layer of the cylindrical absorbent article.

2. An absorbent article for a medical treatment or menstruation according to claim 1, wherein said elimination means is formed of a string, with both end of the string being tied with each other, with said flat absorbent article being in the longitudinal direction into the elimination string, with part of the tired string being exposed to one side of the widthwise direction of the flat absorbent article.

3. An absorbent article for a medical treatment or menstruation according to claim 2, wherein said cylindrical absorbent article is used as a tampon for menstruation.

4. An absorbent article for a medical treatment or menstruation according to claim 3, wherein a front end portion of the cylindrical absorbent article is formed in a circular convex shape.

5. An absorbent article for a medical treatment or menstruation according to claim 2, wherein said cylindrical absorbent article is used as a surgical operation absorption fabric.

6. An absorbent article for a medical treatment or menstruation according to claim 1, wherein said cylindrical absorbent article is used as a tampon for menstruation.

7. An absorbent article for a medical treatment or menstruation according to claim 6, wherein a front end portion of the cylindrical absorbent article is formed in a circular convex shape.

8. An absorbent article for a medical treatment or menstruation according to claim 1, wherein said cylindrical absorbent article is used as a surgical operation absorption fabric.

* * * * *